(12) United States Patent
Kim

(10) Patent No.: US 6,914,099 B2
(45) Date of Patent: Jul. 5, 2005

(54) WATER ABSORBENT RESIN PARTICLES OF CROSSLINKED CARBOXYL-CONTAINING POLYMERS WITH LOW MONOMER CONTENT

(75) Inventor: Young-Sam Kim, Midland, MI (US)

(73) Assignee: Dow Global Technologies Inc., Midland, MI (US)

( * ) Notice: Subject to any disclaimer, the term of this patent is extended or adjusted under 35 U.S.C. 154(b) by 17 days.

(21) Appl. No.: 10/450,432

(22) PCT Filed: Dec. 18, 2001

(86) PCT No.: PCT/US01/48879

§ 371 (c)(1),
(2), (4) Date: Oct. 10, 2003

(87) PCT Pub. No.: WO02/053605

PCT Pub. Date: Jul. 11, 2002

(65) Prior Publication Data

US 2004/0068057 A1 Apr. 8, 2004

Related U.S. Application Data

(60) Provisional application No. 60/258,980, filed on Dec. 29, 2000.

(51) Int. Cl.[7] .............................. C08C 19/20; C08F 8/42
(52) U.S. Cl. ................. 525/343; 525/329.5; 525/329.7; 525/330.3; 525/367; 526/317.1; 526/240; 526/229; 526/343; 524/832; 524/827
(58) Field of Search .................. 524/832, 827; 525/329.5, 329.7, 330.3, 367, 343; 526/317.1, 240, 229

(56) References Cited

U.S. PATENT DOCUMENTS

| | | | |
|---|---|---|---|
| 4,286,082 A | 8/1981 | Tsubakimoto et al. | 526/240 |
| 4,295,987 A | 10/1981 | Parks | 252/194 |
| 4,340,706 A | 7/1982 | Obayashi et al. | 526/207 |
| 4,506,052 A | 3/1985 | Furukawa et al. | 524/357 |
| 4,610,678 A | 9/1986 | Weisman et al. | 604/368 |
| 4,654,039 A | 3/1987 | Brandt et al. | 604/368 |
| 4,666,983 A | 5/1987 | Tsubakimoto et al. | 525/119 |
| 4,734,478 A | 3/1988 | Tsubakimoto et al. | 527/300 |
| RE32,649 E | 4/1988 | Brandt et al. | 604/368 |
| 5,075,344 A | 12/1991 | Johnson | 521/140 |
| 5,145,906 A | 9/1992 | Chambers et al. | 524/732 |
| 5,342,899 A | 8/1994 | Graham et al. | 525/301 |
| 5,373,066 A | 12/1994 | Rebre et al. | 525/387 |
| 5,506,324 A | 4/1996 | Gartner et al. | 526/318.41 |
| 5,629,377 A | 5/1997 | Burgert et al. | 524/832 |

FOREIGN PATENT DOCUMENTS

| | | | |
|---|---|---|---|
| GB | 2119384 | 11/1983 | C08J/3/24 |

OTHER PUBLICATIONS

WO 2004/003036, Burgert, Josef H., "Process for the preparation of iron ion containing water–absorbent polymers with low residual monomer content.", May 19, 2003. Designating US.

Derwent Abstract 1978–60669A, German Patent 2,706,135, E. Barthell et al., Aug. 17, 1978.

Derwent Abstract 1980–46551C, Japanese Patent 55082104, G. L. Goeke et al., Jun. 20, 1980.

Derwent Abstract 2000–595479, European Patent 1035139, M. Gotsche et al., Sep. 13, 2000.

*Primary Examiner*—Tatyana Zalukaeva

(57) ABSTRACT

Superabsorbent polymers having reduced levels of residual monomer are produced using a peroxodisulfate salt.

17 Claims, No Drawings

WATER ABSORBENT RESIN PARTICLES OF CROSSLINKED CARBOXYL-CONTAINING POLYMERS WITH LOW MONOMER CONTENT

This application claims the benefit of Provisional application Ser. No. 60/258,980, filed Dec. 29, 2000.

This invention relates to water-absorbent particles of crosslinked carboxyl-containing polymers that have low residual monomer content.

Superabsorbent polymers, also referred to as aqueous fluid absorbent polymers or water-absorbent resin particles, are primarily used in personal care products such as, for example, baby diapers, adult incontinence products and feminine hygiene products. In such applications, water-absorbent resin particles are incorporated into absorbent structures that contain synthetic and/or natural fibers in woven or nonwoven structures, such as fluff pads. The materials used in such structures ideally are capable of quickly absorbing aqueous fluids and distributing them to desired components of the whole absorbent structure. The structures, in the absence of water-absorbent resin particles, have limited absorption capacity, are bulky due to the large amount of material needed to provide acceptable absorption capacity, and do not retain fluid under pressure. A means for improving the absorbency and fluid retention characteristics of such absorbent structures is to incorporate water-absorbent resin particles that imbibe fluids to form a swollen hydrogel material.

The water-absorbent resin particles quickly absorb fluids and retain them to prevent leakage and give the absorbent structure a "dry feel" even when wetted. See U.S. Pat. No. 4,610,678 for examples of such resins. See also Brandt U.S. Pat. Nos. 4,654,039 and Re. 32,649, which disclose a process for the preparation of water-absorbent resins and the use of known crosslinking agents for such resins, and also Parks U.S. Pat. No. 4,295,987 and Japan Patent 55-82104. A variation of the basic process is taught in GB Patent 2,119,384, which discloses a post-polymerization surface crosslinking process in which the previously polymerized absorbent resin powder is mixed with crosslinkers, preferably polyalcohols, a solvent and water, to coat the resin surface, and heated to temperatures in the range of 90 to 300° C. to crosslink the surface. U.S. Pat. No. 5,506,324 discloses water-absorbent resin particles comprising polymers containing carboxyl moieties which are crosslinked using $C_{2-10}$ polyhydric hydrocarbons which are ethoxylated with from 2 to 8 ethylene oxide units per hydroxyl moiety of the ethylene oxide chain wherein the hydroxyl moiety at the end of each chain is esterified with a $C_{2-10}$ unsaturated carboxylic acid or ester thereof. In a preferred embodiment, the water-absorbent resin particles are subjected to heat-treatment after drying and sizing.

A basic problem with commercially available water-absorbent resin particles has been the presence of residual monomers, which represent process inefficiency. Accordingly, it would be desirable to have a process for preparing a water-absorbent polymer product with reduced residual monomer.

Various methods for lowering residual monomer content are known in the art. European Patent Publication 505 163 relates to a method of reducing residual (meth)acrylic acid present in polyacrylic acid water-absorbent gel polymers that comprises treating the polymers with a combination of a surfactant having a certain HLB and a vinyl addition compound that can react with a vinylic double bond. Examples of the vinyl addition compound include sulfites and bisulfites. An aqueous solution of the additives is mixed with the water absorbent polymer in the form of swollen gel or beads, or dry polymer.

U.S. Pat. No. 5,629,377 discloses water-absorbent resin particles with high absorption values and low residual monomer levels. The resin particles are prepared by polymerizing unsaturated carboxyl containing monomers in the presence of a chlorine- or bromine-containing oxidizing agent to form a hydrogel that is then heated at a temperature of from 170° C. to 250° C., preferably from 210° C. to 235° C. Alternatively, the chlorine- or bromine-containing oxidizing agent may be added to the polymerized hydrogel. The method is effective for improving absorbency, for example, centrifuge capacity and absorbency under load (AUL). However, the high heat treat temperature needed to activate the chlorine- or bromine-containing oxidizing agent is detrimental for various reasons, including energy cost and loss of moisture.

Therefore, it would be desirable to provide a novel method for the preparation of water-absorbent resin particles having a low residual monomer level, which method avoids these disadvantages.

This invention relates to a process for the preparation of water-absorbent resin particles which comprises:

(I) polymerizing a polymerization mixture comprising:
 (a) one or more ethylenically unsaturated carboxyl-containing monomers,
 (b) one or more crosslinking agents,
 (c) optionally one or more comonomers copolymerizable with the carboxyl-containing monomer, and
 (d) a polymerization medium, to form a crosslinked hydrogel, (II) contacting the crosslinked hydrogel with a peroxodisulfate salt, (III) comminuting the hydrogel to particles prior to or after the peroxodisulfate salt is added in step (II), and (IV) drying the hydrogel to form resin, wherein step (II) is conducted in the substantial absence of a combination of surfactant and a material capable of adding across or reacting with a vinyl double bond so as to form reaction products which are incapable of vinyl polymerization via free radical initiation.

Another aspect of the invention is a water-absorbent resin particle prepared by the process of this invention. Yet another aspect of the invention is an absorbent structure comprising water-absorbent resin particles of this invention and at least one of a woven or nonwoven structure of paper, synthetic fibers, or natural fibers.

The water-absorbent resin particles of the present invention have, after drying but before heat treatment, a low residual monomer content, preferably less than 300 ppm, more preferably less than 200 ppm and most preferably less than 100 ppm, based on weight of polymer solids. The heat-treated water-absorbent resin particles of the present invention also have a low residual monomer content, preferably less than 500 ppm, more preferably less than 400 ppm and most preferably less than 300 ppm, based on the weight of polymer solids.

The polymers of the resin particles are prepared from one or more ethylenically unsaturated carboxylic acids, ethylenically unsaturated carboxylic acid anhydrides or salts thereof. Additionally, the polymers may include comonomers known in the art for use in water-absorbent resin particles or for grafting onto the water-absorbent resins including comonomers such as an acrylamide, an acrylonitrile, a vinyl pyrrolidone, a vinyl sulphonic acid or a salt thereof, a cellulosic monomer, a modified cellulosic monomer, a polyvinyl alcohol or a starch hydrolyzate. If used, the comonomer comprises up to 25 weight percent of the monomer mixture.

Preferred unsaturated carboxylic acid and carboxylic acid anhydride monomers include the acrylic acids such as, for example, acrylic acid, methacrylic acid, ethacrylic acid, α-chloroacrylic acid, α-cyano acrylic acid, β-methyl acrylic acid (crotonic acid), α-phenyl acrylic acid, β-acryloyloxy propionic acid, sorbic acid, α-chloro sorbic acid, angelic acid, cinnamic acid, p-chloro cinnamic acid, beta-styrenic acrylic acid (1-carboxy-4-phenyl butadiene-1,3), itaconic acid, citraconic acid, mesaconic acid, glutaconic acid, maleic acid, fumaric acid and maleic acid anhydride. More preferably the starting monomer is acrylic acid, methacrylic acid, or a salt thereof, with acrylic acid or a salt thereof being most preferred.

The use herein of the prefix "(meth)" with generic terms, such as, for example, "acrylic acid", or "acrylate" is meant to broaden the terms to include both acrylate and methacrylate species. Thus, the term "(meth)acrylic acid monomer" includes acrylic acid and methacrylic acid.

Incorporated into the resin are polyvinyl crosslinkers commonly known in the art for use in water-absorbent resin particles. Preferred compounds having at least two polymerizable double bonds include: di- or polyvinyl compounds such as divinyl benzene, divinyl toluene, divinyl xylene, divinyl ether, divinyl ketone and trivinyl benzene; di- or polyesters of unsaturated mono- or polycarboxylic acids with polyols, such as di- or tri-(meth)acrylic acid esters of polyols such as ethylene glycol, diethylene glycol, triethylene glycol, tetra ethylene glycol, propylene glycol, dipropylene glycol, tri propylene glycol, tetra propylene glycol, trimethylol propane, glycerin, polyoxyethylene glycols and polyoxypropylene glycols; unsaturated polyesters that can be obtained by reacting any of the above-mentioned polyols with an unsaturated acid such as maleic acid; di- or polyesters of unsaturated mono- or polycarboxylic acids with polyols derived from the reaction of $C_2$–$C_{10}$ polyhydric alcohols with 2 to 8 $C_2$–$C_4$ alkylene oxide units per hydroxyl group, such as tri methylol propane hexaethoxyl triacrylate; di- or tri-(meth)acrylic acid esters that can be obtained by reacting polyepoxides with (meth)acrylic acid; bis(meth) acrylamides such as N,N-methylene-bisacrylamide; carbamyl esters that can be obtained by reacting polyisocyanates such as tolylene diisocyanate, hexamethylene diisocyanate, 4,4'-diphenyl methane diisocyanate and NCO-containing prepolymers obtained by reacting such diisocyanates with active hydrogen atom-containing compounds with hydroxyl group-containing monomers, such as di-(meth)acrylic acid carbamyl esters obtainable by reacting the above-mentioned diisocyanates with hydroxyethyl (meth)acrylate; di- or poly(meth)allyl ethers of polyols such as alkylene glycols, glycerol, polyalkylene glycols, polyoxyalkylene polyols and carbohydrates such as polyethylene glycol diallyl ether, allylated starch, and allylated cellulose; di- or poly-allyl esters of polycarboxylic acids, such as diallyl phthalate and diallyl adipate; and esters of unsaturated mono- or polycarboxylic acids with mono(meth)allyl ester of polyols, such as allyl methacrylate or (meth)acrylic acid ester of polyethylene glycol monoallyl ether.

Among the more preferred classes of crosslinkers are bis(meth)acrylamides; allyl(meth)acrylates; di- or polyesters of (meth)acrylic acid with polyols such as diethylene glycol diacrylate, trimethylol propane triacrylate, and polyethylene glycol diacrylate; and di- or polyesters of unsaturated mono- or poly-carboxylic acids with polyols derived from reaction of $C_1$–$C_{10}$ polyhydric alcohols with 2 to 8 $C_2$–$C_4$ alkylene oxide units per hydroxyl group, such as ethoxylated trimethylol propane triacrylate. More preferably the crosslinking agents correspond to Formula 1:

$$R^1(\!\!-\!\!(R^2O)_n\!\!-\!\!C(O)R^3)_x \qquad \text{Formula 1}$$

wherein:

$R^1$ is a straight- or branched-chain polyalkoxy radical with 1 to 10 carbon atoms, optionally substituted with one or more oxygen atoms in the backbone, having x valences;

$R^2$ is independently in each occurrence an alkylene group of 2 to 4 carbon atoms;

$R^3$ is independently in each occurrence a straight- or branched-chain alkenyl moiety with 2 to 10 carbon atoms;

n is a number from 1 to 20; and x is a number from 2 to 8.

In the most preferred embodiment the polyvinyl crosslinker corresponds to Formula 1 wherein $R^1$ is derived from trimethylolpropane, $R^2$ is ethylene (—$CH_2CH_2$—), $R^3$ is vinyl (—CH═$CH_2$—), the average value of n is from 2 to 6, and x is 3. In particular the most preferred polyvinyl crosslinker is highly ethoxylated trimethylolpropane triacrylate, containing an average of 15 to 16 ethoxyl groups per molecule of trimethylolpropane. Crosslinkers corresponding to Formula 1 are available from Craynor under the trademark Craynor and from Sartomer under the trademark Sartomer. Generally, the crosslinkers described by Formula 1 are found as a mixture of materials described by the formula and by-products resulting from the preparation process.

The non-vinyl crosslinkers of this invention are agents having at least two functional groups capable of reacting with the carboxyl groups of the polymer, such as glycerin, polyglycols, ethylene glycol, digylcidyl ether, and aliamines. Many examples of these compounds are given in U.S. Pat. Nos. 4,666,983 and 4,734,478 which teach the application of such agents to the surface of absorbent resin powder followed by heating to crosslink surface chains and improve absorption capacity and absorption rate. Additional examples are given in U.S. Pat. No. 5,145,906, which teaches post-crosslinking with such agents. In the current invention, the non-vinyl crosslinkers preferably are added homogeneously to the polymerization mixture at the start of the process. Preferred non-vinyl crosslinkers include hexane diamine, glycerin, ethylene glycol diglycidyl ether, ethylene glycol diacetate, polyethylene glycol 400, polyethylene glycol 600, and polyethylene glycol 1000. The most preferred non-vinyl crosslinkers are polyethylene glycol 400 and polyethylene glycol 600.

The dimodal crosslinkers of this invention are agents that have at least one polymerizable vinyl group and at least one functional group capable of reacting with carboxyl groups. The term "dimodal crosslinkers" is employed to distinguish these from normal vinyl crosslinkers, because they use two different modes of crosslinking. Examples of dimodal crosslinkers include hydroxyethyl methacrylate, polyethylene glycol monomethacrylate, glycidyl methacrylate, and allyl glycidyl ether. Many examples of these type of compounds are given in U.S. Pat. Nos. 4,962,172 and 5,147,956, which teach the manufacture of absorbent films and fibers by (1) preparing linear copolymers of acrylic acid and hydroxyl containing monomers, (2) forming solutions of these copolymers into the desired shapes, and (3) fixing the shape by heating the polymer to form ester crosslinks between the pendant hydroxyl and carboxyl groups. In the current invention, the dimodal crosslinkers preferably are added homogeneously to the polymerization mixture at the start of the process. Preferred dimodal crosslinkers include hydroxyethyl (meth)acrylate, polyethylene glycol 400 monomethacrylate, glycidyl methacrylate. The most preferred dimodal crosslinker is hydroxyethyl (meth)acrylate.

The total amount of all crosslinkers present is sufficient to provide a resin with good absorptive capacity, good absorption under load, and a low percent of extractable materials. Preferably the crosslinkers are present in an amount of at least 1,000 parts per million by weight based on the amount of the polymerizable monomer present, more preferably at least 2,000 parts per million and most preferably at least 4,000 parts per million. Preferably the crosslinkers are present in an amount of 50,000 parts per million or less by weight based upon the amount of the polymerizable monomer present, more preferably 20,000 parts per million or less and most preferably 15,000 parts per million or less.

In those embodiments of the invention that utilize a blend of polyvinyl crosslinkers with non-vinyl and or dimodal crosslinkers, the effect on heat-treated capacity of all three types of crosslinkers is additive in nature. That is, if the amount of one crosslinker is increased the amount of another must be decreased to maintain the same overall heat-treated capacity. In addition, the proportion of the crosslinker components within the blend may be varied to achieve different resin properties and processing characteristics. In particular the polyvinyl crosslinkers of the invention are typically more expensive than non-vinyl or dimodal crosslinkers. Therefore the overall cost of the resin is reduced if a greater proportion of the crosslinker blend is the less expensive non-vinyl and or dimodal crosslinkers. However, the non-vinyl and dimodal crosslinkers of the invention function essentially as latent crosslinkers. That is, the crosslinking imparted to the resin by these agents is essentially not developed or seen until after the heat-treatment step. Little, if any, toughness is added to the hydrogel immediately after polymerization when latent crosslinkers are employed. This is an important concern for those processes for which a "tough" gel is desirable.

If too little of the total crosslinker blend is composed of polyvinyl crosslinker the polymerized hydrogel may not have sufficient toughness to be easily ground, processed, and dried. For this reason the proportion of polyvinyl crosslinker in the total crosslinker blend is preferably at least sufficient to produce a hydrogel that has enough toughness to be readily ground, processed, and dried. This toughness is inversely proportional to the centrifuge capacity of the resin after drying but before heat-treatment. The exact amount of polyvinyl crosslinker required in the blend to achieve this level of toughness will vary, but is enough to provide a centrifuge capacity of the resin, after drying but before heat-treatment, of preferably 45 g/g or less, more preferably 40 g/g or less, and most preferably 35 g/g or less.

Conventional additives that are well known in the art, such as surfactants, may be incorporated into the polymerization mixture. Polymerization can be accomplished under polymerization conditions in an aqueous or nonaqueous polymerization medium or in a mixed aqueous/nonaqueous polymerization medium. Polymerization accomplished by processes which employ nonaqueous polymerization media may use various inert hydrophobic liquids which are not miscible with water, such as hydrocarbons and substituted hydrocarbons including halogenated hydrocarbons as well as liquid hydrocarbons having from 4 to 20 carbon atoms per molecule, including aromatic and aliphatic hydrocarbons, as well as mixtures of any of the aforementioned media.

In one embodiment, the resin particles are prepared by contacting the reactive monomers and crosslinkers of the invention in an aqueous medium in the presence of a free radical or oxidation reduction (redox) catalyst system and a chlorine- or bromine-containing oxidizing agent under conditions such that a crosslinked hydrophilic resin is prepared. In another embodiment, the resin particles are prepared by contacting the reactive monomers and crosslinkers of the invention in an aqueous medium in the presence of a free radical or oxidation-reduction (redox) catalyst system under conditions such that a crosslinked hydrophilic resin is prepared. As used herein, aqueous medium means water, or water in admixture with a water-miscible solvent. Examples of water-miscible solvents include lower alcohols and alkylene glycols. Preferably the aqueous medium is water.

The monomers and crosslinkers are preferably dissolved, dispersed or suspended in a suitable polymerization medium, such as, for example, the aqueous medium at a concentration level of 15 weight percent or greater, more preferably 25 percent or greater, and most preferably 29 percent or greater. The monomers and crosslinkers are preferably dissolved, dispersed or suspended in the aqueous medium.

The free radical initiator may be any conventional water soluble free radical polymerization initiator including, for example, peroxygen compounds such as sodium, potassium and ammonium persulfates, caprylyl peroxide, benzoyl peroxide, hydrogen peroxide, cumene hydroperoxide, tertiary butyl diperphthalate, tertiary butyl perbenzoate, sodium peracetate and sodium percarbonate.

Conventional redox initiator systems can also be utilized. These systems can be formed by combining the foregoing peroxygen compounds with reducing agents, such as, for example, sodium bisulfite, sodium thiosulphate, L- or iso-ascorbic acid or a salt thereof, or ferrous salts. Up to 5 mole percent of the initiator can be employed, based on the total moles of polymerizable monomer present. More preferably from 0.001 to 0.5 mole percent of initiator is employed, based on the total moles of polymerizable monomer in the aqueous medium.

An important aspect of the present invention is the addition of the peroxodisulfate salt. The counterion of the peroxodisulfate salt can be any counterion that does not significantly interfere with the preparation of the resin particles or their performance. Preferably, the counterion is an alkali metal ion or an ammonium ion. More preferred counterions are the alkali metals, with potassium and sodium even more preferred. Preferably, the peroxodisulfate salt is employed in an amount of from 0.001 to 15 parts by weight, more preferably form 0.03 to 3.0 parts by weight and most preferably from 0.15 to 0.8 parts by weight, all based on one hundred parts by weight of the total amount of components (a), (b) and (c) of the polymerization mixture.

In an embodiment wherein the dried hydrogel is subjected to heat-treatment, the process is desirably conducted in the presence of a chlorine- or bromine-containing oxidizing agent in addition to the peroxodisulfate salt. The use of a chlorine- or bromine-containing oxidizing agent results in a higher post heat-treatment absorption capacity than is obtainable without it. The utilization of a chlorine- or bromine-containing oxidizing agent also has the effect of further reducing the residual monomer content in the final heat-treated product compared with that observed when the resin is heat-treated without the chlorine- or bromine-containing oxidizing agent. Preferred chlorine- or bromine-containing oxidizing agents are bromates and chlorates and chlorites, the chlorates and bromates being even more preferred. The counterion of the bromate, chlorate or chlorite salt can be any counterion which does not significantly interfere with the preparation of the resin particles or their performance. Preferably, the counterions are alkaline earth metals ions or alkali metal ions. More preferred counterions are the alkali metals, with potassium and sodium being even more preferred. The chlorine containing oxidizing agents are most preferred.

The chlorine- or bromine-containing oxidizing agent is present in an amount such that after heat-treatment the desired balance of resin properties is achieved. Preferably, at least 10 ppm by weight of a chlorine- or bromine-containing oxidizing agent, based on the total weight of monomers (a) and (c) is employed, more preferably at least 50 ppm, and even more preferably at least 100 ppm and most preferably at least 200 ppm. Desirably, the amount of a chlorine- or bromine-containing oxidizing agent employed is 2000 ppm or less by weight based on the total weight of monomers (a) and (c), more desirably 1000 ppm or less, preferably 800 ppm or less and most preferably 500 ppm or less. The chlorine- or bromine-containing oxidizing agent is preferably dissolved or dispersed in the polymerization mixture prior to initiation of the polymerization. However, it may also be applied as an aqueous solution to the hydrogel, together with or in addition to the peroxodisulfate salt.

The process of the invention may be performed in a batch manner wherein all of the reaction materials are contacted and the reaction proceeds, or it may take place with the continuous addition of one or more of the components during the reaction period. The polymerization mixture, including the polymerization medium, is subjected to polymerization conditions that are sufficient to produce the water-absorbent resin particles.

Preferably, the reaction is performed under an inert gas atmosphere, for example, under nitrogen or argon. The reaction may be performed at any temperature at which polymerization occurs, preferably at least 0° C., more preferably at least 25° C. and most preferably at least 50° C.

The reaction is conducted for a time sufficient to result in the desired conversion of monomer to crosslinked hydrophilic resin. Preferably, the conversion is at least 85 percent, more preferably at least 95 percent and most preferably at least 98 percent.

Preferably, at least 25 mole percent of the carboxylic acid units of the hydrophilic resin are neutralized with base, even more preferably at least 50 percent and most preferably at least 65 percent. This neutralization may be performed after completion of the polymerization. In a preferred embodiment the starting monomer mix has carboxylic acid moieties which are neutralized to the desired level prior to polymerization. The final polymer or the starting monomers may be neutralized by contacting them with a salt-forming cation. Examples of such salt-forming cations include alkaline metal, ammonium, substituted ammonium and amine based cations. Preferably, the polymer is neutralized with an alkali metal hydroxide such as, for example, sodium hydroxide or potassium hydroxide, or an alkali metal carbonate such as, for example, sodium carbonate or potassium carbonate.

It is also possible to prepare the resin of the current invention by adding recycled "fines" to the polymerization mixture. See WO 92/20723. "Fines" are generally considered to include, but are not limited to, the fraction of water-absorbent resin particle that passes through a 140 mesh screen when the dried and ground product is screened prior to heat-treatment. The amount of fines added to the polymerization mixture is, on a total solids basis, preferably less than 12 weight percent, more preferably less than 10 weight percent, and most preferably less than 8 weight percent.

It is also possible to carry out the polymerization process using multiphase polymerization techniques such as inverse emulsion polymerization or inverse suspension polymerization procedures. In the inverse emulsion polymerization or inverse suspension polymerization procedures, the aqueous reaction mixture as hereinbefore described is suspended in the form of tiny droplets in a matrix of a water-immiscible, inert organic solvent, such as cyclohexane. Polymerization occurs in the aqueous phase, and suspensions or emulsions of this aqueous phase in an organic solvent permit better control of the exothermic heat of polymerization and further provide the flexibility of adding one or more of the aqueous reaction mixture components in a controlled manner to the organic phase.

Inverse suspension polymerization procedures are described in greater detail in Obayashi et al., U.S. Pat. No. 4,340,706; and in Flesher et al. U.S. Pat. No. 4,506,052. When inverse suspension polymerization or inverse emulsion polymerization techniques are employed, additional ingredients such as surfactants, emulsifiers and polymerization stabilizers may be added to the overall polymerization mixture. When any process employing organic solvent is utilized, it is important that the hydrogel-forming polymer material recovered from such processes be treated to remove substantially all of the excess organic solvent. Preferably, the hydrogel-forming polymers contain no more than 0.5 percent by weight of residual organic solvent.

During polymerization, the resin of the invention generally absorbs the entire aqueous reaction medium to form a hydrogel. The resin is removed from the reactor in the form of an aqueous hydrogel. The term "hydrogel" as used herein refers to a water swollen water-absorbent resin or resin particles. In preferred embodiments, such hydrogels comprise 15 to 50 percent by weight resin, with the remainder comprising water. In a more preferred embodiment the hydrogel comprises 25 to 45 percent resin. The hydrogel is preferably processed into a particulate shape during the polymerization reaction process by the agitator in the reactor to facilitate the removal of the hydrogel from the reactor. Preferred particle sizes of the hydrogel range from 0.001 to 25 cm, more preferably from 0.05 to 10 cm. In multiphase polymerization, the water-absorbent resin hydrogel particles may be recovered from the reaction medium by azeotropic distillation and/or filtration followed by drying. If recovered by filtration, then some means of removing the solvent present in the hydrogel must be used. Such means are commonly known in the art.

After removal from the reactor, the hydrogel resin is subjected to comminution, such as, for example, by a convenient mechanical means of particle size reduction, such as grinding, chopping, cutting and extrusion. The size of the gel particles after particle size reduction should be such that homogeneous drying of the particles can occur. Preferred particle sizes of the hydrogel range from 0.5 to 3 mm. This particle size reduction can be performed by any means known in the art that gives the desired result. Preferably, the particle size reduction is accomplished by chopping.

The hydrogel may be contacted with the peroxodisulfate salt prior to, or after, comminuting the hydrogel to particles but before any moisture is removed. If the hydrogel is substantially dried prior to application of the peroxodisulfate salt a significant reduction of the monomer content in the resin particles is not seen.

It is preferred to distribute the peroxodisulfate salt substantially uniformly through the hydrogel. The mixing of the hydrogel and the peroxodisulfate salt occurs by diffusion of the peroxodisulfate salt into the wet polymer gel. Additional mixing measures may be applied to improve the distribution of the peroxodisulfate salt within the hydrogel. Suitable mixing methods include, for example, stirring and agitation. It is preferred to add the peroxodisulfate salt prior to the comminuting step since intensive mixing inherently occurs during comminuting the hydrogel to particles.

The peroxodisulfate salt may be added to the hydrogel in any suitable form such as, for example, as an aqueous solution, as a dry salt, or in the form of swollen "fines" pretreated with an aqueous peroxodisulfate solution. It is preferred to apply the peroxodisulfate salt as an aqueous solution or in the form of peroxodisulfate-treated fines.

When an aqueous peroxodisulfate salt solution is used, it is preferably sprayed on the crosslinked hydrogel. The concentration of the peroxodisulfate salt solution is not critical, as long as sufficient distribution of the peroxodisulfate salt within the hydrogel can be ensured. Desirable concentrations of the peroxodisulfate salt in water range from 0.1 to 35 weight percent. The amount of water used to prepare the peroxodisulfate salt solution ranges from 0.1 to 999 parts by weight per hundred parts by weight of polymer solids.

If an aqueous solution of a chlorine- or bromine-containing oxidizing agent is added to the hydrogel, it may be applied in a manner similar to that of the peroxodisulfate salt solution, that is, it may be contacted with the hydrogel prior to or after comminution, together with the peroxodisulfate salt or as a separate solution. The preferred concentration of the chlorine- or bromine-containing oxidizing agent in water is from 0.1 to 10 weight percent.

In another preferred embodiment, small water-absorbent resin particles ("fines") are treated with the peroxodisulfate salt solution as defined above. The fines preferably pass through a 45 mesh screen. On contact with the peroxodisulfate solution the dry fines rehydrate and swell. The swollen fines are then thoroughly mixed with the crosslinked hydrogel obtained in step (I) of the present process. It is preferred to use 0.1 to 25 parts by weight of fines rehydrated with a solution of 0.001 to 15 parts by weight peroxodisulfate salt in 0.1 to 999 parts by weight water, all based on one hundred parts by weight of polymer solids. The fines are preferably obtained by polymerizing a polymerization mixture as defined in step (I). In a preferred embodiment of the invention, the peroxodisulfate-treated swollen small water-absorbent resin particles are prepared in a separate step from dry small resin particles, and the small resin particles are obtained by polymerizing a polymerization mixture as defined in step (I), wherein the dry resin particles are rehydrated by contacting them with an aqueous solution of the peroxodisulfate salt.

If the peroxodisulfate salt is applied to the hydrogel after comminution, then additional components, including reducing agents, water-insoluble fine inorganic particles, surfactants, organic solvents, organic mineral oil and mixtures thereof, may be added to avoid sticking and/or improve the flow properties of the gel particles and/or to achieve better distribution of the peroxodisulfate salt. If the peroxodisulfate salt is applied prior to comminution, the addition of those additives is not necessary. It is even preferred to contact the peroxodisulfate salt with the hydrogel in absence of any of those additives since the incorporation of additives may have a negative effect on absorbent polymer properties.

After contact with the peroxodisulfate salt, optionally in combination with a chlorine- or bromine-containing oxidizing agent, and comminution, the hydrogel resin particles are subjected to drying conditions to remove the remaining polymerization medium and any dispersing liquid, including the optional solvent and substantially all of the water. Desirably, the moisture content of the polymer after drying to remove the polymerization medium and any dispersing liquid is between zero and 20 weight percent, preferably between 5 and 10 weight percent.

The temperature at which the drying takes place is a temperature high enough such that the polymerization medium and liquid, including water and optional solvent, is removed in a reasonable time period, yet not so high so as to cause degradation of the resin particles. Preferably, the temperature of the resin particles during drying is 180° C. or less. Desirably, the temperature during drying is 100° C. or above, preferably 120° C. or above and more preferably 150° C. or above.

The drying time should be sufficient to remove substantially all of the water and optional solvent. Preferably, a minimum time for drying is at least 10 minutes, with at least 15 min being preferred. Preferably, the drying time is 60 min or less, with 25 min or less being more preferred. In a preferred embodiment, drying is performed under conditions such that water, and optional solvent, volatilizing away from the absorbent resin particles is removed. This removal can be achieved by vacuum techniques or by passing inert gases or air over or through the layers of resin particles. In a preferred embodiment, drying occurs in dryers in which heated air is blown through or over layers of the resin particles. Preferred dryers are fluidized beds or belt dryers. Alternatively, a drum dryer may be used. In another alternative, the water may be removed by azeotropic distillation. Such techniques are well known in the art.

During drying, the water-absorbent resin particles may form agglomerates and may then be subjected to comminution, such as, for example, by mechanical means for breaking up the agglomerates. In a preferred embodiment, the dried water-absorbent resin particle agglomerates are subjected to mechanical particle reduction means. Such means can include chopping, cutting and/or grinding. The object is to produce a product with a particle size acceptable in the ultimate end use. In a preferred embodiment, the resin particle agglomerates are chopped and then ground. The final particle size is preferably 2 mm or less, more preferably 0.8 mm or less. Preferably the particles have a size of at least 0.01 mm, more preferably at least 0.05 mm. The dried water-absorbent resin particles of the present invention can be used as the substrate polymer for further surface crosslinking treatment, for example, using polyvalent cations like aluminum ions and/or using one of the crosslinkers mentioned above as a surface crosslinker by coating the particles followed by heating at elevated temperatures.

In a preferred embodiment after drying and optional particle size reduction, the resin particles are subjected to a heat-treatment step. Heat-treatment of the resin provides a beneficial increase in the absorption under load (AUL) of the water-absorbent resin, particularly the AUL under higher pressures. Suitable devices for heat-treatment include, but are not limited to, rotating disc dryers, fluid bed dryers, infrared dryers, agitated trough dryers, paddle dryers, vortex dryers, and disc dryers. One of ordinary skill in the art would vary the time and temperature of heat-treatment as appropriate for the heat transfer properties of the particular equipment used, and for the particular polymer properties desired.

The time period and temperature of the heat-treatment step are chosen such that the absorption properties of the resin are improved as desired. The resin particles are desirably heated at a temperature of at least 170° C., more desirably at least 180° C., preferably at least 200° C. and most preferably at least 220° C. No improvement in the absorption properties is observed below 170° C. The temperature should not be so high as to cause the resin particles to degrade. Preferably, the temperature is 250° C. or below and more preferably 235° C. or below.

The resin particles are heated to the desired heat-treatment temperature and preferably maintained at such temperature for at least 1 min and more preferably at least 5 min and most preferably at least 10 min. Below 1 min no improvement in properties is generally seen. If the heating time is too long it becomes uneconomical and there is a risk that the resin particles maybe damaged. Preferably, the resin particles are maintained at the desired temperature for 60 min or less, preferably 40 min or less. No significant improvement in properties is noticed if heat treatment lasts more than 60 minutes. The properties of the resin particles can be adjusted and tailored by adjustment of the temperature and the time of the heating step.

After heat-treatment, the resin particles may be difficult to handle due to static electricity. It may be desirable to rehumidify the particles to reduce or eliminate the effect of the static electricity. Methods of humidification of dry resins are well known in the art. In a preferred mode, the dry particles are contacted with water vapor. The dry particles are contacted with a sufficient amount of water to reduce or eliminate the effects of the static electricity, yet not so much so as to cause the particles to agglomerate. Preferably, the dry particles are humidified with at least 0.3 percent by weight of water and more preferably at least 5 percent by weight of water. The dry particles preferably are humidified with 10 percent or less by weight of water and more preferably 6 percent or less by weight of water. Optionally, agglomeration prevention or rehydration additives may be added to the crosslinked hydrophilic resin. Such additives are well known in the art and include surfactants and inert inorganic particles such as silica; see, for example, U.S. Pat. Nos. 4,286,082 and 4,734,478; and DE 2706135.

The resin particles according to the present invention have an exceptionally low level of residual monomers due the treatment with the peroxodisulfate salt. A considerable advantage of the present process is that the peroxodisulfate salt provides a beneficial decrease in residuals in both heat-treated and non-heat-treated resin particles. Heating the resin particles normally increases the amount of residual monomers due to thermally induced cleavage via a reverse Michael reaction. However, peroxodisulfate-treated, heat treated resin particles show a lower level of residuals versus heat-treated resin without the peroxodisulfate treatment.

The water-absorbent resin particles of this invention can be used in any use wherein absorption and binding of aqueous fluids is desired. In a preferred embodiment, the water-absorbent resin particles of this invention are mixed into or attached to a structure of absorbent material prepared from synthetic or natural fibers or paper based woven or nonwoven fibers. The woven or nonwoven structure functions as a mechanism for wicking and transporting fluids via capillary action to the water-absorbent resin particles, which bind and retain the fluids. Accordingly, the particles of the invention can be used in articles such as, for example, diapers, adult incontinence structures, and sanitary napkins.

The absorbent structures of the present invention comprise means to contain water-absorbent resin particles. Any means capable of containing the described water-absorbent resin particles, which means is further capable of being positioned in a device such as an absorbent garment, is suitable for use in the present invention. Many such containment means are known to those skilled in the art. For example, the containment means may comprise a fibrous matrix such as an airlaid or wetlaid web of cellulosic fibers, a meltblown web of synthetic polymeric fibers, a spun-bonded web of synthetic polymeric fibers, a coformed matrix comprising cellulosic fibers and fibers formed from a synthetic polymeric material, airlaid heat-fused webs of synthetic polymeric material or open-celled foams, or combinations of these. In one embodiment, it is preferred that the fibrous matrix comprise less than 10, preferably less than 5, weight percent of cellulosic fibers.

Further, the containment means may comprise a support structure, such as a polymeric film, on which the water-absorbent resin particles is affixed. The water-absorbent resin particles may be affixed to one or both sides of the support structure, which may be water-pervious or water-impervious.

Because the water-absorbent resin particles present in the absorbent structures of the present invention can be present in high concentrations, the absorbent structures of the present invention can be relatively thin and have a relatively small volume and still function in as desired.

The absorbent structures according to the present invention are suited to absorb many fluids including body fluids such as, for example, urine, menses, and blood and are suitable for use in absorbent garments such as diapers, adult incontinent products and bed pads; in catamenial devices such as sanitary napkins and tampons; and in other absorbent products such as, for example, wipes, bibs and wound dressings. Accordingly, in another aspect, the present invention relates to an absorbent garment comprising an absorbent structure as described above.

The following examples are included to illustrate the invention, and are not to be construed as limiting its scope. All parts and percentages are by weight unless otherwise indicated.

Particle Size Distribution (PSD) Analysis of Fines

Fines that were used for preparing of peroxodisulfate treated rehydrated and swollen fines (PRSF) are obtained from a commercial plant during the manufacturing processes of a superabsorbent polymer when the dried and ground product is screened prior to heat-treatment (HT). The size fractions of the fines materials used were evaluated 8 times. The particle size distributions of the fines are given below in Table 1.

TABLE 1

Particle Size Distribution of Fines

| No. of Evaluation | Particle Size Distribution (percent) | | | |
|---|---|---|---|---|
| | >0.315 mm | >0.212 mm | >0.150 mm | <0.150 mm |
| 1 | 0.3 | 1.8 | 20.8 | 77.1 |
| 2 | 0.2 | 2.1 | 21.0 | 76.7 |
| 3 | 0.3 | 2.0 | 19.8 | 77.9 |
| 4 | 0.3 | 1.8 | 21.1 | 76.8 |
| 5 | 0.4 | 2.1 | 20.1 | 77.4 |
| 6 | 0.3 | 2.0 | 21.7 | 75.8 |
| 7 | 0.3 | 2.2 | 22.9 | 74.6 |
| 8 | 0.3 | 2.0 | 22.5 | 75.2 |

Peroxodisulfate Salt Solution Treatment

Peroxodisulfate salt solutions are freshly prepared before the experiments were carried out. In a typical peroxodisulfate solution treatment experiment, the desired amount of peroxodisulfate salt was dissolved in water, then the peroxodisulfate salt solution was sprayed onto hydrogel in a tray, while the mixture is mixed roughly by hand. In some cases, gel was shaken while spraying the solution onto hydrogel in a plastic container or in a vinyl bag. This spraying and mixing process sufficiently mixed the peroxodisulfate solution and gel prior to gel mincing. The obtained peroxodisulfate solution treated gel was then minced by a laboratory extruder (a household mincer, MADO GmbH, Germany) through the die plate (6 mm die size) and the minced gel was then dried in a forced-air laboratory oven (HERAEUS) at 170° C. for two hours.

Heat-Treatment Procedures

Heat-Treatment Method 1: 20 g of resin (30/50 mesh size fraction) were put into a 10 cm diameter aluminum tray, and the tray was then placed in a forced-air oven (HERAEUS) that had been pre-heated to the desired temperature for the desired time.

Heat-Treatment Method 2: In some experiments, the heating was performed by pre-heating a zone with a hot air-gun (laboratory fluid bed). Once the target temperature was reached and stabilized, approximately 20 g of resin sample (30/50 mesh size fraction) were placed in the zone and a contact thermometer was placed in contact with the sample. The temperature of the sample was monitored until it stabilized at the target temperature. The sample was maintained at the target temperature for the desired time.

Method for Evaluation of Residual Monomer

The samples of the powder superabsorbent resin polymer prior to and after heat treatment having a particle size fraction between 30 and 50 mesh were used for analysis of residual monomer content. Residual monomer concentration was measured in ppm (parts per million) based on weight of dry polymer. The term "before heat-treatment" refers to the properties of the polymer after drying and sizing but before any heat-treatment. The term "after heat-treatment" refers to the properties of the polymer after heat-treatment.

To determine the amount of residual acrylic acid, 1.000 g of each sample was shaken for 16 h in 185 g of an aqueous 0.9 percent NaCl solution; and the resulting slurries were then filtered using Watman No. 3 filter paper. A sample of the filtrate was injected into a liquid chromatograph to determine monomeric acrylic acid using UV detection at 205 nm. The residual monomer was calculated by comparing the peak area of the acrylic acid peak to that of a standard sample.

EXAMPLES

In all of the following experiments, the control sample was the corresponding polymer without peroxodisulfate salt addition. All examples marked as "*" are comparative experiments and not examples of the present invention.

The Examples 1 to 10 illustrate the effects of peroxodisulfate treated rehydrated and swollen fines (PRSF) on residuals in hydrogels containing high residual monomer concentration ('high dimer gel') which were prepared using high dimer content acrylic acid. High dimer content acrylic acid was prepared intentionally in the laboratory by simple aging of acrylic acid at room temperature for a prolonged time. In Examples 1 to 10, the peroxodisulfate effect is shown in the presence (Examples 1 to 5) or absence (Examples 6 to 10) of chlorate.

Polymerization Using Laboratory Glass Reactor

A high dimer content acrylic acid, containing 3492 ppm dimer, was used to prepare SAP gels containing a chlorate level of 263 ppm (based on the sum weight of acrylic acid, HE-TMPTA and PEG 600) or 0 ppm chlorate (Table 2). Polymerizations were conducted using a glass laboratory reactor (reactor volume 300 mL) without agitation. The detailed recipes of the both trials are given below in Table 2. The degree of acid neutralization for both recipes was 68 percent. The polymerization procedures are further described below.

TABLE 2

Polymerization Recipe with and without Chlorate

| Ingredients Component | Conc. percent wt. | Chlorate Recipe Weight (g) | Non Chlorate Recipe Weight (g) |
|---|---|---|---|
| Acrylic acid | 99 | 439.07 | 439.07 |
| Sodium hydroxide | 20 | 829.36 | 829.36 |
| Water |  | 212.15 | 213.31 |
| HE-TMPTA[(1)] | 100 | 1.32 | 1.32 |
| PEG 600[(2)] | 100 | 1.32 | 1.32 |
| Versenex ® 80[(3)] | 40.2 | 0.55 | 0.55 |
| Hydrogen peroxide | 15 | 1.05 | 1.05 |
| Sodium chlorate | 10 | 1.16 | 0.00 |
| Sodium peroxodisulfate | 10 | 7.46 | 7.46 |
| Ascorbic acid | 1.0 | 6.59 | 6.59 |

[(1)]Highly ethoxylated trimethylolpropane triacrylate
[(2)]Polyethylene glycol with an average molecular weight of 600 g/mol, available from Clariant Company.
[(3)]Penta sodium salt of diethylene triamine pentaacetic acid Preparation of Monomer Mix Acrylic acid (299.57 g) was added to 829.36 g of 20 wt percent sodium hydroxide aqueous solution in a plastic beaker which was cooled with ice. The acrylic acid was added portion-wise so that the temperature did not exceed 30° C. Versenex® 80 (Trademark of The Dow Chemical Company, penta sodium salt of diethylene triamine pentaacetic acid, 40.2 wt percent aqueous) (0.55 g) was added to the pre-neutralized mix. Then, 212.15 g of deionized water was poured into the mix. The pre-mix was added to a beaker, and 1.32 g HE-TMPTA as vinyl crosslinker was dissolved in 139.5 g acrylic acid and added to the monomer mix. As non vinyl crosslinker, 1.32 g polyethylene glycol (PEG 600) was dissolved in the mix. For the recipe containing chlorate, 1.16 g of 10 wt percent sodium chlorate aqueous solution was added to the monomer mix. If no chlorate was added to the mix, 1.16 g of deionized water were used instead. The mix was stirred well after every addition.

Polymerization

The monomer mixture (250 g) was placed in a 300 ml round bottom flask equipped with a flange at the top. The flange was sealed with a lid which contained four openings, two of which were reserved for the thermometer and the nitrogen gas supply, while one opening was connected to the vent system and the fourth one was sealed with a septum. The monomer mixture was purged for 30 minutes with a nitrogen stream (150 liter/h) to remove traces of oxygen. The desired amount of peroxodisulfate salt was added as a 0.1 wt percent peroxodisulfate solution directly to the monomer mix. The nitrogen bubbling was reduced (50 liter/h), and the initiators were added to the prepared monomer mix in following sequence: 1.05 g of 15 wt percent hydrogen peroxide solution, 7.46 g of 10 wt percent sodium peroxodisulfate, and 6.59 g of 1 wt percent ascorbic acid solution.

The polymerization for chlorate and non-chlorate recipe was started at room temperature. After introduction of the ascorbic acid, the monomer mix became slightly turbid. The mix increased in viscosity and was more cloudy about three minutes after initiation. Gel formation was seen at approximately 50° C., and the gel still appeared slightly turbid. The gel became slightly transparent when it exceeded 50° C. It took approximately. 20–25 min until the polymerization mix reached 70° C., regardless of the presence of chlorate. After 70° C. was reached, the flask was placed in a water-bath for 60 min at 70° C. Then, the reactor was opened and a mass of aqueous polymer gel (one gel piece) was collected which was then subsequently cut into small pieces, followed by mincing in the laboratory extruder having a die diameter of 6 mm.

Treatment of Peroxodisulfate Treated Rehydrated and Swollen Fines (PRSF)

Peroxodisulfate treated rehydrated and swollen fines (PRSF) were freshly prepared before the experiments were conducted. The desired amount of sodium peroxodisulfate (Table 3) was dissolved in 22.5 g of water, corresponding to 25.7 parts per hundred parts of polymer solids, then the solution was mixed with 2.5 g of fines (2.9 parts based on hundred parts of polymer solids) which swelled quickly. In Examples 1 to 10, PRSF was mixed with gel roughly by hand in a plastic tray to give a homogeneous mixture of gel and PRSF, and the resulting treated gel was minced by a laboratory extruder through the die plate (6 mm die size), followed by drying in a laboratory oven (HERAEUS) at 170° C. for two hours. For the control and comparative samples, minced gel that had not been subjected to peroxodisulfate treatment was employed.

The dried materials were ground using the laboratory grinder (household mixer, Moulinette) and sieved using a 30 and 50 mesh sieves. Approximately 20 g of the fraction were heat-treated in the laboratory fluid bed at 190° C. for 30 minutes (heat-treatment method 2). Samples (30/50 mesh) were analyzed for residuals both for before and after HT.

TABLE 3

Treatment Agents and Heat Treatment Conditions (PRSF Treatments in 'High Dimer Gels')

| Example | chlorate | Treatment Agent | Amount of Treatment Agent in g (pphps$^a$) | Amount of fines in g/amount of water in g | HT Temp/Time |
|---|---|---|---|---|---|
| 1$^{C*}$ | 263 ppm | — | — | — | 190° C./30 min |
| 2$^{C*}$ | 263 ppm | — | — | 2.5 g/22.5 g | 190° C./30 min |
| 3 | 263 ppm | Na$_2$S$_2$O$_8$ | 0.375 g (0.43 pphps) | 2.5 g/22.5 g | 190° C./30 min |
| 4 | 263 ppm | Na$_2$S$_2$O$_8$ | 0.625 g (0.71 pphps) | 2.5 g/22.5 g | 190° C./30 min |
| 5 | 263 ppm | Na$_2$S$_2$O$_8$ | 1.250 g (1.43 pphps) | 2.5 g/22.5 g | 190° C./30 min |
| 6$^{C*}$ | — | — | — | — | 190° C./30 min |
| 7$^{C*}$ | — | — | — | 2.5 g/22.5 g | 190° C./30 min |
| 8 | — | Na$_2$S$_2$O$_8$ | 0.375 g (0.43 pphps) | 2.5 g/22.5 g | 190° C./30 min |
| 9* | — | Na$_2$S$_2$O$_8$ | 0.625 g (0.71 pphps) | 2.5 g/22.5 g | 190° C./30 min |
| 10* | — | Na$_2$S$_2$O$_8$ | 1.250 g (1.43 pphps) | 2.5 g/22.5 g | 190° C./30 min |

$^C$control sample
*comparative experiment, not an embodiment of the invention
$^a$pphps = parts per hundred parts of polymer solids

TABLE 4

Results for Residuals before and after Heat Treatment (PRSF Treatment in High Dimer gel)

| Example | Residuals before HT in ppm (relative change in percent) | Residuals after HT in ppm (relative change in percent) |
|---|---|---|
| 1$^{C*}$ | 563 (0 percent) | 979 (0 percent) |
| 2$^{C*}$ | 656 (+16.5 percent) | 1111 (+13.5 percent) |
| 3 | 492 (−12.6 percent) | 868 (−11.3 percent) |
| 4 | 479 (−14.9 percent) | 821 (−16.1 percent) |
| 5 | 432 (−23.3 percent) | 694 (−29.1 percent) |
| 6$^{C*}$ | 885 (0 percent) | 1403 (0 percent) |
| 7$^{C*}$ | 739 (−16.5 percent) | 1346 (−4.1 percent) |
| 8 | 583 (−34.2) | 1156 (−17.6 percent) |
| 9 | 542 (−38.8 percent) | 1050 (−25.2 percent) |
| 10* | 519 (−41.4 percent) | 987 (−29.7 percent) |

$^C$control sample
*comparative experiment, not an embodiment of the invention

As seen from Examples 1 to 10 in Table 4, the polymerization of high dimer content acrylic acid resulted in very high residual monomer content. Irrespective of heat treatment, the presence of chlorate in general clearly shows an advantage compared to the non chlorate containing recipe with regard to the residual monomer values.

It is also clearly seen from Examples 1 to 10 in Table 4 that the PRSF method provides significantly improved amounts of residuals in the resin particles versus the control product, regardless of the presence of chlorate. The relative improvement in residual monomer reduction was slightly more effective when peroxodisulfate treatment was applied to non chlorate-process high dimer recipe gel. However, the absolute residual monomer values were more favorable in the chlorate containing high dimer gels. The results clearly demonstrate that the effect of the present invention is observed even for polymer prepared from acrylic acid with very high dimer content. It is well known that dimer content in acrylic acid may increase due to prolonged transport time and due to storage at elevated temperature during warm weather. The results shown above are very positive in the economic sense since low quality acrylic acid, that is, partly high dimer content acrylic acid, can be used for polymerization without any additional technically complicated processing and/or purification steps.

Example 11

Feed Polymer Gel and Control Sample

Improved superabsorbent polymer products of the present invention were prepared by adding peroxodisulfate salt solution to gel. Experiments were conducted using DRYTECH® S230R superabsorbent polymer gel (Trademark of The Dow Chemical Company). DRYTECH® S230R is available from Dow Deutschland GmbH & Co. OHG, Germany. It has a degree of neutralization of about 68 mol percent. DRYTECH® S230R contains sodium chlorate and the typical polymerization recipe used is comparable to that given in Table 2 ("chlorate recipe").

Water-swollen superabsorbent hydrogel from the DRYTECH® S230R process was taken prior to gel mincing for use in experiments 12 to 20 in Table 5 below. The hydrogel was not sticky and was tough enough to be easily treated gel were then minced by a laboratory mincer through the die plate (6 mm die size) and the peroxodisulfate treated and minced gel was then dried in the laboratory oven (HERAEUS) at 170° C. for two hours. The dried materials were ground using the laboratory grinder (household mixer, Moulinette) and sieved using a 30 and a 50 mesh sieve set (that is, particle size distribution between 0.595 mm and 0.297 mm). Resin particles (20 g) were placed in an aluminum tray and heat-treated in an air-forced laboratory oven (Examples 12 to 20) (heat-treatment method 1) at 200° C. for 60 min. The resulting heat-treated samples are evaluated for residual monomers, and the results are given in Table 5.

TABLE 5

Gel Treatment using Peroxodisulfate Salt Solution and Peroxodisulfate Salt Treated Rehydrated and Swollen Fines (PRSF) and Results for Residuals before and after Heat Treatment (HT)

| Example | Treatment Agent | Amount of Treatment Agent in g (pphps[a]) | Amount of fines in g/ water in g | HT Temp/Time | Residuals before HT in ppm (relative change in percent) | Residuals after HT in ppm (relative change in percent) |
|---|---|---|---|---|---|---|
| 12[C*] | — | — | — | 200° C./60 min | 273 ppm (0 percent) | 515 ppm (0 percent) |
| 13 | $Na_2S_2O_8$/solution[(1)] | 0.5 g (0.14 pphps) | 0 g/90 g | 200° C./60 min | 144 ppm (−47.3 percent) | 365 ppm (−29.1 percent) |
| 14 | $Na_2S_2O_8$/solution | 1.0 g (0.28 pphps) | 0 g/90 g | 200° C./60 min | 139 ppm (−49.1 percent) | 368 ppm (−28.5 percent) |
| 15 | $Na_2S_2O_8$/solution | 2.0 g (0.56 pphps) | 0 g/90 g | 200° C./60 min | 103 ppm (−62.3 percent) | 337 ppm (−34.6 percent) |
| 16 | $Na_2S_2O_8$/solution | 4.0 g (1.11 pphps) | 0 g/90 g | 200° C./60 min | 93 ppm (−65.9 percent) | 322 ppm (−37.5 percent) |
| 17 | $Na_2S_2O_8$/fines | 0.5 g (0.14 pphps) | 10 g/90 g | 200° C./60 min | 159 (41.8 percent) | 382 (−25.5 percent) |
| 18 | $Na_2S_2O_8$/fines | 1.0 g (0.28 pphps) | 10 g/90 g | 200° C./60 min | 148 (−45.8 percent) | 360 (−29.8 percent) |
| 19 | $Na_2S_2O_8$/fines | 2.0 g (0.56 pphps) | 10 g/90 g | 200° C./60 min | 107 (−60.8 percent) | 330 (−35.7 percent) |
| 20 | $Na_2S_2O_8$/fines | 4.0 g (1.11 pphps) | 10 g/90 g | 200° C./60 min | 104 (−72.1 percent) | 334 (−34.9 percent) |

[C]control sample
*comparative examples being not examples of this invention
[a]pphps = parts per hundred parts of polymer solids (= total amount of monomers and crosslinker)
[(1)]solution = peroxodisulfate ion solution treatment
[(2)]fines = peroxodisulfate ion treatment using peroxodisulfate treated rehydrated and swollen fines (PRSF)

for use in experiments 12 to 20 in Table 5 below. The hydrogel was not sticky and was tough enough to be easily handled in the form of small particulate gel pieces; it is used as the base polymer for the following experiments.

Examples 12 to 20

Peroxodisulfate Salt Solution Treatment and Processing of the Hydrogel with Peroxodisulfate Solution Example 12 was a control sample and was not peroxodisulfate salt treated. Examples 13 to 16 relate to the treatment of gel with aqueous peroxodisulfate salt solution. Examples 17 to 20 relate to the treatment of gel with peroxodisulfate salt treatment in the form of PRSF. The PRSF were prepared by adding the corresponding amounts of peroxodisulfate salt (Table 5) dissolved in 90 g of water (25 parts per hundred parts of polymer solids) with 10 g of dry fines (2.8 parts per hundred parts of polymer solids). The resulting PRSF were added to 1,000 g of non-extruded gel from Example 11 and mixed thoroughly by hand. The peroxodisulfate salt solution treated gel and the PRSF It is clearly seen from Examples 13 to 20 in Table 5 that the present method provides significantly improved, reduced amounts of residuals in the resin particles compared to the control product (Example 12). The relative improvement ranges between approximately 40 and 70 percent for non heat-treated samples, depending on the amount of peroxodisulfate salt added. A significant improvement is also seen when the samples are heat-treated. Heating samples led to increased residual values in all samples. Consequently, products with a high value of residuals were obtained. However, the peroxodisulfate treated samples again show the most improved residual monomer concentration, with the relative improvement ranging between approximately 30 and 40 percent.

It is also seen from Table 5, comparing Examples 13–16 to Example 17–20, that the effect of adding peroxodisulfate salt treated rehydrated and swollen fines to the hydrogel is approximately the same as adding the same amount of peroxodisulfate salt in aqueous solution.

Examples 21 to 25

Other Solution Treatment and Processing of the Treated Hydrogel

Example 21 is a control sample and was not peroxodisulfate salt treated. In Examples 22 to 25, the amounts of the treatment agents indicated in Table 6 were dissolved in 180 g of water. The solutions were sprayed on 2,000 g gel from Example 11 and mixed thoroughly by hand. The solution treated gel was then minced by a laboratory mincer through the die plate (6 mm die size) and the resulting minced gel was then dried in the laboratory oven (HERAEUS) at 170° C. for two hours. The dried materials were ground using the laboratory grinder (household mixer, Moulinette) and sifted using a 30 and a 50 mesh sieve set (that is, particle size distribution between 0.595 mm and 0.297 mm). The resin particles (20 g) were placed in an aluminum tray and heat-treated using heat-treatment method 1 at 190° C. for 35 min. The resulting heat-treated samples are evaluated for residual monomers, and the results are given in Table 6.

TABLE 6

Treatment Agents and Heat Treatment Conditions and Results for Residuals before and after Heat Treatment

| Example | Treatment Agent | Amount of Treatment Agent in g (pphps$^a$) | Amount of water in g | HT Temp/Time | Residuals before HT in ppm (relative change in percent) | Residuals after HT in ppm (relative change in percent) |
|---|---|---|---|---|---|---|
| 21$^{C*}$ | — | — | — | 190° C./35 min | 313 ppm (0 percent) | 410 ppm (0 percent) |
| 22 | Na$_2$S$_2$O$_8$ | 5.0 g (0.69 pphps) | 180 g | 190° C./35 min | 193 ppm (−38.3 percent) | 310 ppm (−24.4 percent) |
| 23* | H$_2$SO$_3$ | 50 g$^b$ (0.42 pphps) | 180 g | 190° C./35 min | 495 ppm (+58.1 percent) | 570 ppm (+39.0 percent) |
| 24* | Na$_2$S$_2$O$_5$ | 6.0 g (0.83 pphps) | 180 g | 190° C./35 min | 274 ppm (−12.5 percent) | 355 ppm (−13.4 percent) |
| 25* | H$_2$O$_2$ | 10 g$^d$ (0.42 pphps) | 180 g | 190° C./35 min | 355 ppm (+14.5 percent) | 435 ppm (+6.1 percent) |

$^C$control sample
*comparative examples being not examples of this invention
$^a$pphps = parts per hundred parts of polymer solids (= total amount of monomers and crosslinker)
$^b$of a 6 percent aqueous solution
$^d$of a 30 percent aqueous solution In Examples 22 to 25 the treatment of the present invention is compared with other treatments including reducing agents, for example, sulfurous acid (Example 23), sulfite (Example 24) or an oxidizing agent like hydrogen peroxide (Example 25). The sample treated with the peroxodisulfate salt (Example 22) was found to give the most effectively reduced residual monomer value.

What is claimed is:

1. A process for the preparation of water-absorbent resin particles, the process comprising:
    (I) polymerizing a polymerization mixture comprising:
        (a) one or more ethylenically unsaturated carboxyl-containing monomers,
        (b) one or more crosslinking agents,
        (c) optionally one or more comonomers copolymerizable with the carboxyl-containing monomer, and
        (d) a polymerization medium, to form a crosslinked hydrogel,
    (II) contacting the crosslinked hydrogel with a peroxodisulfate salt,
    (III) comminuting the hydrogel to particles prior to or after the peroxodisulfate salt is added in step (II), and
    (IV) drying the hydrogel to form resin,
    wherein step (II) is conducted in the substantial absence of a combination of surfactant and a material capable of adding across or reacting with a vinylic double bond so as to form reaction products which are incapable of vinylic polymerization via free radical initiation.

2. The process of claim 1 wherein the amount of peroxodisulfate salt is from 0.001 to 15 parts by weight per hundred parts by weight of the total amount of components (a), (b) and (c) of the polymerization mixture.

3. The process of claim 1 wherein the peroxodisulfate salt is in the form of an aqueous solution.

4. The process of claim 1 wherein at least part of the salt is employed as fines that were pretreated with an aqueous peroxodisulfate salt solution.

5. The process of claim 1 wherein the hydrogel is processed into particles having particle sizes of from 0.05 to 10 cm during the polymerization reaction in step (1).

6. The process of claim 1 further comprising heating the dried hydrogel from step (IV) to a temperature of from 170 to 250° C. for from 1 to 60 minutes.

7. The process of claim 6 wherein the heating is conducted in the presence of a chlorine-or bromine-containing oxidizing agent.

8. The process of claim 7 wherein the chlorine- or bromine-containing oxidizing agent is dissolved or dispersed in the polymerization mixture in an amount of from 10 to 2,000 ppm, based on the total weight of monomers, prior to initiation of the polymerization in step (1).

9. The process of claim 1 wherein the peroxodisulfate salt is contacted with the hydrogel in step (II) prior to comminuting the hydrogel in step (III).

10. The process of claim 9 wherein the contacting of the peroxodisulfate salt with the hydrogel in step (II) is conducted in the substantial absence of at least one of the following additives: reducing agents, water-insoluble fine inorganic particles, surfactants, organic solvents, and mineral oil.

11. The process of claim 1 wherein the peroxodisulfate salt is an alkali metal peroxodisulfate or ammonium peroxodisulfate.

12. The process of claim 7 wherein the chlorine- or bromine-containing oxidizing agent is selected from the group consisting of sodium chlorate, potassium chlorate, sodium bromate, potassium bromate, sodium chlorite and potassium chlorite or mixtures thereof.

13. The process of claim 1 wherein the peroxodisulfate salt is sodium persulfate.

14. A process for the preparation of water-absorbent resin particles, the process comprising:
   (I) polymerizing a polymerization mixture comprising:
      (a) acrylic acid,
      (b) one or more crosslinking agents,
      (c) optionally one or more comonomers copolymerizable with acrylic acid, and
      (d) an aqueous polymerization medium, to form a crosslinked hydrogel,
   (II) contacting the crosslinked hydrogel with a peroxodisulfate salt,
   (III) comminuting the hydrogel to particles prior to adding the peroxodisulfate salt in step (II), and
   (IV) drying the hydrogel to form resin,
wherein step (II) is conducted in the substantial absence of a combination of surfactant and a material capable of adding across or reacting with a vinylic double bond so as to form reaction products which are incapable of vinylic polymerization via free radical initiation.

15. The process of claim 14 wherein the peroxodisulfate salt is sodium persulfate.

16. The process of claim 14 wherein the amount of peroxodisulfate salt is from 0.001 to 15 parts by weight per hundred parts by weight of the total amount of components (a), (b) and (c) of the polymerization mixture.

17. A process for the preparation of water-absorbent resin particles, the process comprising:
   (I) polymerizing a polymerization mixture comprising:
      (a) acrylic acid,
      (b) one or more crosslinking agents according to Formula I:

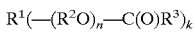

$$R^1(\text{---}(R^2O)_n\text{---}C(O)R^3)_k$$

wherein: $R^1$ is a straight- or branched-chain polyalkoxy radical with 1 to 10 carbon atoms, optionally substituted with one or more oxygen atoms in the backbone; $R^2$ is independently in each occurrence an alkylene group of 2 to 4 carbon atoms; $R^3$ is independently in each occurrence a straight- or branched-chain alkenyl moiety with 2 to 10 carbon atoms; n is a number from 1 to 20; and x is a number from 2 to 8
      (c) optionally one or more comonomers copolymerizable with the carboxyl-containing monomer, and
      (d) an aqueous polymerization medium, to form a crosslinked hydrogel,
   (II) contacting the crosslinked hydrogel with 0.001 to 15 parts by weight per hundred parts by weight of the total amount of an alkali metal or ammonium peroxodisulfate salt,
   (III) comminuting the hydrogel to particles prior to or after the peroxodisulfate salt is added in step (11), and
   (IV) drying the hydrogel to form resin,
wherein step (II) is conducted in the substantial absence of a combination of surfactant and a material capable of adding across or reacting with a vinylic double bond so as to form reaction products which are incapable of vinylic polymerization via free radical initiation.

* * * * *